United States Patent [19]

Tsuji et al.

[11] Patent Number: 4,800,747
[45] Date of Patent: Jan. 31, 1989

[54] METHOD OF MEASURING OXYGEN IN SILICON

[75] Inventors: Katsuya Tsuji; Takeshi Yamada; Hiroshi Uchihara, all of Kyoto, Japan

[73] Assignee: Horiba, Ltd., Miyanohigashi, Japan

[21] Appl. No.: 157,852

[22] Filed: Feb. 18, 1988

[30] Foreign Application Priority Data

Feb. 28, 1987 [JP] Japan ................... 62-47086

[51] Int. Cl.4 ............................................. G01N 31/12
[52] U.S. Cl. ............................................. 73/19; 422/80
[58] Field of Search .................. 73/19; 422/78, 80

[56] References Cited

U.S. PATENT DOCUMENTS 2,964,389 12/1960 Bennett et al. ..................... 422/80
3,293,902 12/1966 Kraus ................................. 73/19
3,751,965 8/1973 Kraus ................................. 73/19
3,812,705 5/1974 Boillot ............................... 73/19
3,899,627 8/1975 Sitek et al. ...................... 73/19 X
3,946,228 3/1976 Biermann ......................... 73/19 X
4,098,576 7/1978 Judge ............................... 73/19 X

*Primary Examiner*—Stewart J. Levy
*Assistant Examiner*—Joseph W. Roskos
*Attorney, Agent, or Firm*—Price, Gess & Ubell

[57] ABSTRACT

A heat melting type gas extraction apparatus is employed to measure oxygen in a silicon sample. A double graphite crucible is first heated, in the absence of the sample or a flux metal, to extract oxygen therein. The flux metal is then added to the crucible and heated to extract oxygen therein. The sample is then added, melted, and heated to produce a sample gas for analysis.

16 Claims, 2 Drawing Sheets

METHOD OF MEASURING OXYGEN IN SILICON

BACKGROUND OF THE INVENTION

1. Field of the Invention

The present invention generally relates to a method of measuring a quantity of oxygen contained in silicon and, in particular, to a quite novel method of measuring oxygen in silicon that provides a handy, speedy and accurately controlled analysis of highly pure single crystalline silicon which is a constituent ingredient in the manufacturing process of, for example, a semiconductor silicon wafer.

2. Description of Related Art

Methods of measuring an absolute quantity of oxygen in silicon have included an activation analysis using charged particles and a vacuum-fusion method. Methods of measuring a relative quantity have included secondary ion mass analysis and infrared absorption analysis.

Of these various kinds of methods, the former three methods require remarkably large and expensive facilities or a long measuring time and much trouble. Accordingly, they are unsuitable for control analysis on an industrial level and hardly used practically; that is, they have been used merely in analysis at an investigation level. Accordingly, in most cases, infrared absorption analysis which merely requires a relatively handy apparatus and measuring operation has been used for control analysis in industry.

However, infrared absorption analysis also has at least the following problems. Since infrared absorption analysis measures a relative quantity, a difficulty in accuracy of measurement occurs in that a relatively large error of measurement is apt to be produced by a thickness effect of the silicon sample, that is, if a thickness of the silicon sample is not strictly equal to that of the standard sample. Also, it is natural in an infrared ray-opaque silicon sample (such as a silicon wafer doped with phosphor, boron, antimony and the like) which has been recently developed for a defect to occur in that infrared absorption analysis cannot be applied at all. Accordingly, in the case where such an infrared ray-opaque silicon sample is an object to be measured, the investigating method, such as secondary ion mass analysis, might be attempted in place of infrared absorption analysis. However, that type of analysis is remarkably disadvantageous in economy, measuring efficiency (usually about 1 hour/1 analysis), operation and the like.

So, the present inventors carried out various kinds of investigation aimed at the development of a method of measuring oxygen in silicon which is a more handy, practical control analysis in place of the conventional infrared absorption analysis and sufficiently applicable even in the case where an infrared ray-opaque silicon sample is an object to be measured. The result was the invention of a method of measuring oxygen in silicon using an extraction analysis of gases in a metal by a heat melting method, which has been already practiced by Horiba, Ltd. And, the present inventors carried out the investigation of the possibility of such method.

According to such a method of measuring oxygen in silicon, as roughly shown in FIG. 2, a graphite crucible "c" is capable of being adjusted in temperature by putting it between an electrode "a" and an electrode "b" in a pressed manner and electrifying it (i.e., passing an electric current "i" through it). Heat is thereby generated at an appointed high temperature to degas the graphite crucible "c" itself. Then, a silicon sample "s" is thrown into the graphite crucible "c" together with a flux metal "m" (for example, metals such as nickel and tin for use in a metallic bath) to extract oxygen contained in the silicon sample "s" in the form of gases combined with carbon (for example, carbon monoxide gas). Subsequently, the extracted gases are introduced into a known gas-concentration analyzer system (not shown) to detect the gas concentration, whereby a quantity of oxygen contained in the silicon sample "s" is measured. That is to say, the same procedure as in the case where an object to be measured is for example iron is adopted.

The method of measuring oxygen in silicon using such a heat melting type gas extraction analysis can be applied also to an infrared ray-opaque silicon sample in principle and can very simply measure a quantity of oxygen contained in the silicon sample. However, various kinds of problems have occurred as follows:

(a) The following reaction makes progress between the graphite crucible "c" and the silicon sample "s" thrown into the graphite crucible "c" to locally produce deteriorated portions (SiC portions having a large electric resistance) in the graphite crucible "c." Therefore, a remarkably large amount of Joule's heat is generated in the deteriorated portions by the electric current "i" passing through the graphite crucible "c" to locally heat the graphite crucible "c" to an abnormally high temperature.

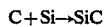

$$C + Si \rightarrow SiC$$

Accordingly, a reaction makes progress between oxygen (so called metal oxide) contained in the graphite crucible "c" itself and a part of the SiC as follows:

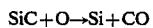

$$SiC + O \rightarrow Si + CO$$

As a result, disadvantages occur in that a blank gas (carbon monoxide gas) leads to a great error of measurement, and the graphite crucible "c" is damaged.

(b) Since also oxygen contained in the flux metal "m" is simultaneously extracted when the silicon sample "s" is heated, a highly pure flux metal "m" containing a very small amount of oxygen must be used. Also, this can lead to a great error in measurement.

(c) Also, an error of measurement due to the rapid evaporation of the silicon sample "s" within the graphite crucible "c" and a greater affect of the gas (carbon monoxide gas) extracted from the vaporized silicon is apt to be produced.

That is to say, practically good results cannot be readily obtained.

SUMMARY OF THE INVENTION

The present invention was achieved as a result of the further investigation aimed at the elimination of the above described kinds of problems in view of the above described actual state of the art. And, it is an object of the present invention to provide a method of measuring oxygen in silicon that can be applied even in the case where an infrared ray-opaque silicon sample is an object to be measured. The method simply and speedily measures a quantity of oxygen contained in the silicon sample with a sufficiently high accuracy, and can be suitably utilized as a simplified industrial control analysis.

To achieve the above described object, a method of measuring oxygen in silicon according to the present invention is characterized by:

(i) heating a double graphite crucible consisting of an outside graphite crucible capable of directly controlling a temperature by electrification to generate heat, and an inside graphite crucible housed in the outside graphite crucible and capable of indirectly controlling a temperature at first at an appointed high temperature to degas the double graphite crucible itself;

(ii) adjusting a temperature of the double graphite crucible at the appointed value and throwing a flux metal into the inside graphite crucible to degas the flux metal;

(iii) adjusting a temperature of the double graphite crucible at values near a melting point of silicon and throwing a silicon sample into the inside graphite crucible to melt the silicon sample in the flux metal and then adjusting the temperature of the double graphite crucible at values relatively higher than the melting point of silicon to extract oxygen contained in the silicon sample in the form of gases combined with carbon; and (iv) introducing the extracted gases into a gas-concentration analyzing system to detect the gas concentration, whereby a quantity of oxygen contained in the silicon sample is measured.

Basically, the conventional heat melting type gas extraction analysis capable of simple and speed measurement in the above described manner is applied to the above described method of measuring oxygen in silicon according to the present invention. The conventional single type graphite crucible is not used, but instead a double graphite crucible consisting of an outside graphite crucible, whose temperature can be directly adjusted by electrification to generate heat (in short, through which an electric current passes). An inside graphite crucible is housed in the outside graphite crucible and is capable of being indirectly adjusted in temperature (through which an electric current hardly passes). In addition, the silicon sample is thrown into the inside graphite crucible. Accordingly, the problem (a), the generation of blank gas and damage to the crucible produced by the use of a single type graphite crucible, does not occur. Even though the following reaction makes progress between the inside graphite crucible and the silicon sample to locally form deteriorated portions (SiC portions), an electric current hardly passes through the inside graphite crucible so that the inside graphite crucible is not heated locally to an abnormally high temperature, unlike the case of the single type graphite crucible. $C + Si \rightarrow SiC$ In addition, since the double graphite crucible itself and the flux metal is degassed before the silicon sample is thrown into the inside graphite crucible, and even though a highly pure flux metal is not prepared, oxygen contained in the flux metal itself can be prevented from causing an error of measurement. Therefore, even if a metal of usual grade is used, the above problem (b) can be solved. Accordingly, the method of measuring oxygen in silicon according to the present invention is economically advantageous.

In addition, the silicon sample is thrown into the double graphite crucible under the condition that the temperature of the double graphite crucible is adjusted at values near the melting point of silicon to melt the silicon sample in the flux metal. Then, the temperature of the double graphite crucible is raised to values relatively higher than the melting point of silicon. Thereby, the temperature of the double graphite crucible during the extraction of gases is controlled in two stages so that the error of measurement due to the rapid evaporation of the silicon sample and the greater affect accompanied by the rapid evaporation of the silicon sample hardly occurs, whereby the above described problem (c) can also be eliminated.

Thus, the synergistic action of the above described effects leads to very simply and speedily carrying out a very highly accurate measurement (with requiring a time of about 1/10 to 1/20 times that required in the case of the secondary ion mass analysis).

BRIEF DESCRIPTION OF THE DRAWINGS

One preferred embodiment of the method of measuring oxygen in silicon according to the present invention is in which.

DESCRIPTION OF THE PREFERRED EMBODIMENTS

One preferred embodiment of a method of measuring oxygen in silicon according to the present invention will be below described with reference to FIGS. 1(a) to (c), which is a flow chart showing a procedure, and FIGS. 1(d) and (e), which is a graph showing a relationship among a temperature within the crucible, quantity of carbon monoxide generated, and time history of detected output.

Figure 1A:
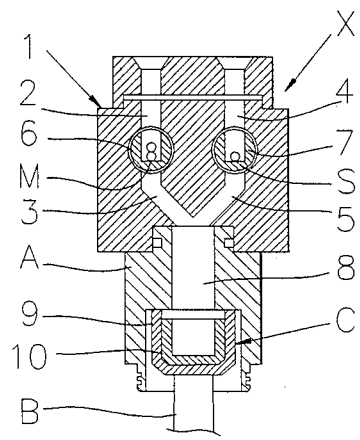
FIGS. 1(a) to (c) is a flow chart showing the procedure.
Figure 1B:
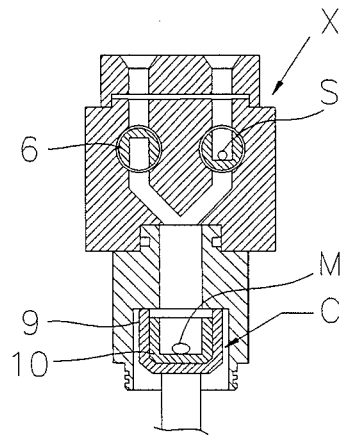
Figure 1C:
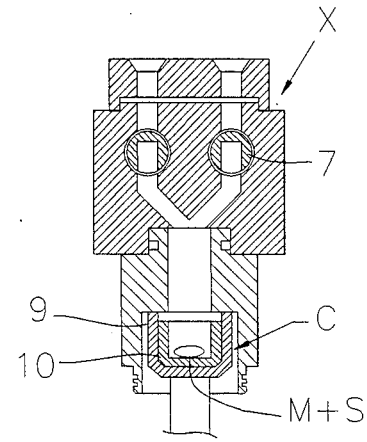

In addition, FIGS. 1(a) to (c) show a heat melting type gas extraction apparatus portion, which is a principal part of the system for measuring oxygen in silicon and to which the present invention is applied. This apparatus is designated by X.

Reference numeral 1 designates a base provided with a port 2 for throwing a flux metal M, a drop passage 3, a port 4 for throwing a silicon sample S, a drop passage 5, a hold/drop change-over member 6 between the port 2 and the drop passage 3, and a hold/drop change-over member 7 between the port 4 and the drop passage 5. Although a rotary type hold/drop change-over member is used in this example, other types of construction, such as a slide type one, may be used.

In addition, reference mark A designates an electrode mounted on a lower side of the base 1, the electrode A being provided with a drop passage 8 communicating with both drop passages 3, 5. The drop passage 8 is provided with a double graphite crucible C at a lower end portion thereof so as to be put between the electrode A and another electrode B in a pressed manner.

This double graphite crucible C consists of an outside graphite crucible 9 whose temperature can be directly adjusted by electrification between both electrodes A, B to generate heat. An inside graphite electrode 10 is housed in the outside graphite crucible 9 and is capable of being indirectly adjusted in temperature. In short, the outside graphite crucible 9 is electrified but the inside graphite crucible 10 is hardly electrified.

The procedure according to the present invention, which is practiced by means of the system for measuring oxygen in silicon comprising the above described heat melting type gas extraction apparatus portion X, is described as follows.

(i) First, as shown in FIG. 1(a), an electric current is passed between both electrodes A, B when the double graphite crucible C is empty. Both the flux metal M and the silicon sample S are not thrown into the double graphite crucible C to heat the whole double graphite crucible C at an appointed high temperature [about 2,800° to 3,000° C. is suitable, as shown in FIG. 1(d)], whereby degassing the double graphite crucible C occurs. Thus, as shown in FIG. 1(e), oxygen, which was contained in the double graphite crucible C itself, is extracted from the inside graphite crucible 10 in the form of carbon monoxide gas. This carbon monoxide gas is not introduced into the analyzing system (not shown here) but is discharged outside of the system so that, as seen from FIG. 1(f), it is not detected.

Figure 1D:
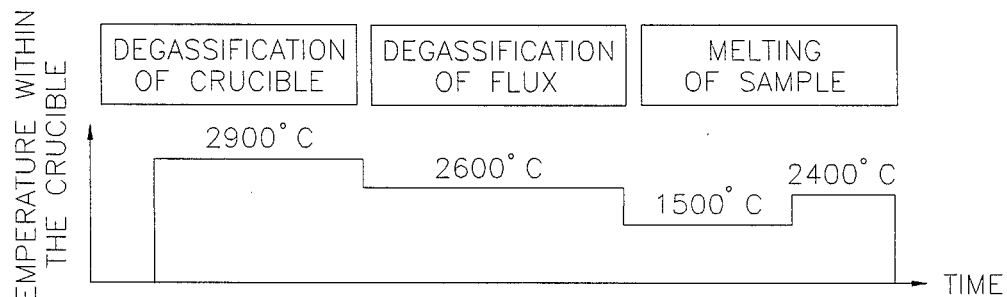
FIGS. 1(d) to (f) is a graph showing a temperature within a crucible, quantity of carbon monoxide generated, and time history of detection output, respectively.
Figure 1E:
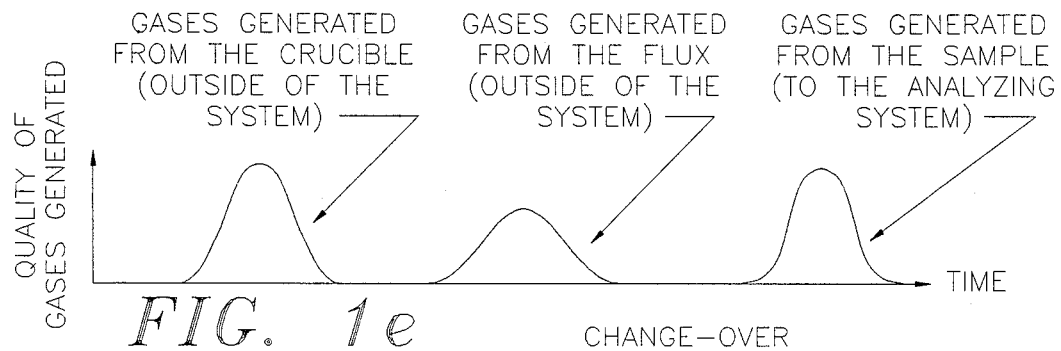
Figure 1F:
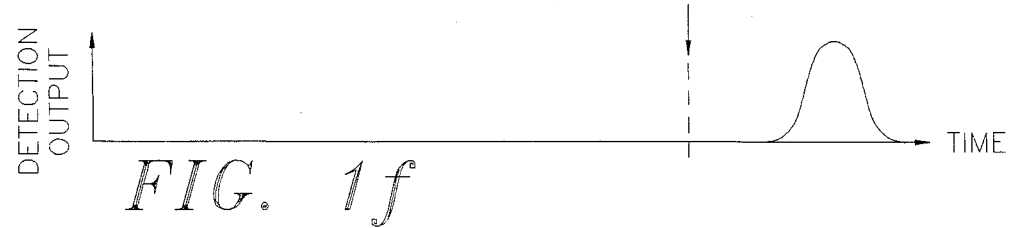
Figure 2:
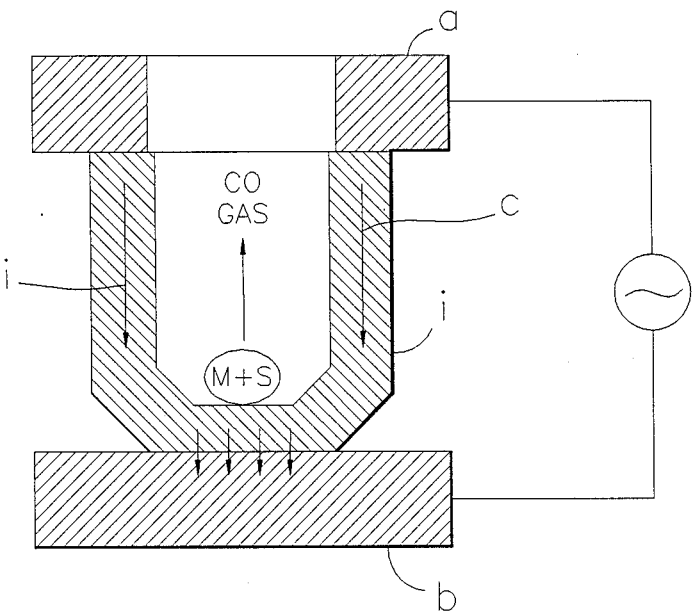
FIG. 2 is a diagram of the conventional heat melting type gas extraction analysis for describing the problems of the prior art and the technical background of the present invention.

(ii) Subsequently, the double graphite crucible C is adjusted to lower the temperature thereof until an appointed value [about 2,500° to 2,700° C. is suitable, as shown in FIG. 1(d)]. Then, as shown in FIG. 1(b), the flux metal M is utilized and, for example, is nickel of 0.3 to 1.5 g and tin of 0 to 2.0 g for the silicon sample S of 0.1 to 0.7 g. Preferably, it is nickel of 0.5 g and tin of 1.0 g for the silicon sample S of about 0.3 g. The flux metal M is thrown into the inside graphite crucible 10 by operating a rotary member 6 that heats and melts the flux metal M, whereby degassing the flux metal M occurs. Thus, as shown in FIG. 1(e), oxygen in the flux metal M is extracted from the inside graphite crucible 10 in the form of carbon monoxide gas. This carbon monoxide gas is discharged outside of the system without being introduced into the analyzing system so that, as seen in FIG. 1(f), it is not detected.

(iii) Successively, the double graphite crucible C is adjusted so as to lower the temperature thereof until values near the melting point of silicon [as shown in FIG. 1(d), about 1,400° to 1,600° C. is suitable]are reached. Then, as shown in FIG. 1(c), the silicon sample S (0.3 g in the above described manner) is thrown into the inside graphite crucible 10 by operating the change-over member 7 and to melt the silicon sample S in the flux metal M. Subsequently, the double graphite crucible C is adjusted so as to raise the temperature thereof until values relatively higher than the melting point of silicon [as shown in FIG. 1(d), about 2,300° to 2,500° C. is suitable]are reached. Thereby, extracting oxygen contained in the silicon sample S in the form of carbon monoxide is accomplished.

(iv) Thus, as shown in FIG. 1(e), oxygen which was contained in the silicon sample S is extracted from within the inside graphite crucible 10 in the form of carbon monoxide gas (sample gas). The extracted carbon monoxide gas is then introduced into a gas-concentration analyzer and a heat-conductivity meter (not shown because they are well known) constructed from a non-dispersive type infrared analyzer and the like by changing-over gas lines, a concentration of carbon monoxide is thus detected, whereby a quantity of oxygen contained in the silicon sample S is measured.

In addition, the carbon monoxide may be additionally oxidized to turn it into carbon dioxide which can be measured. This can be suitably arranged in connection with an analyzer.

As obvious from the above detailed description, according to a method of measuring oxygen in silicon of the present invention, a superior result can be achieved in that this method can be sufficiently applied even to the case where an infrared ray-opaque silicon sample is an object to be measured. A quantity of oxygen contained in the silicon sample can be simply, speedily and accurately measured, whereby this method can be very suitably used as a simple industrial control analysis, by adding various kinds of original devices, such as using a double graphite crucible consisting of an outside graphite crucible whose temperature can be directly adjusted by electrification to generate a heat, and an inside graphite crucible housed in the outside graphite crucible and capable of indirect adjustment in temperature (an electric current hardly passes there-through) as a means for heating and melting the silicon sample to extract oxygen contained in the silicon sample in the form of gases combined with carbon. The heat not only degasses the double graphite crucible itself before the silicon sample is thrown into the inside graphite crucible but also degasses the flux metal, or controlling the temperature of the double graphite crucible during the extraction of gases in two stages, in order to overcome and eliminate various kinds of special problems occurring where this method is applied to the silicon sample in addition to the application of a remarkably simple and speedy heat melting type gas extraction analysis which has been used as a method of analyzing gases in a metal.

What is claimed is:

1. A method of measuring a quantity of oxygen contained in a silicon sample, comprising the steps of:
   heating a double graphite crucible consisting of an outside graphite crucible capable of directly controlling a temperature by electrification to generate heat and an inside graphite crucible housed in said outside graphite crucible capable of indirectly controlling a temperature at first at an appointed high temperature to degas said double graphite crucible itself;
   adjusting a temperature of said double graphite crucible at an appointed value and throwing a flux metal into said inside graphite crucible to degas said flux metal;
   adjusting a temperature of said double graphite crucible at values near a melting point of silicon and throwing a silicon sample into said inside graphite crucible to melt said silicon sample in the flux metal and then adjusting the temperature of said double graphite crucible at values relatively higher than the melting point of silicon to extract oxygen contained in said silicon sample in the form of gases combined with carbon; and
   introducing said extracted gases into a gas-concentration analyzing system to detect the gas concentration, whereby measuring a quantity of oxygen contained in said silicon sample is accomplished.

2. The method of measuring a quantity of oxygen according to claim 1 wherein said double graphite crucible is heated by a pair of electrodes.

3. The method of measuring a quantity of oxygen according to claim 1 wherein said inside graphite crucible is subject to only a slight electrification.

4. The method of measuring a quantity of oxygen according to claim 1 wherein said appointed high temperature is between about 2,800° to 3,000° C.

5. The method of measuring a quantity of oxygen according to claim 4 wherein said appointed value is between about 2,500° to 2,700° C.

6. A method of elemental analysis of a sample, comprising the steps of:
- degassing a double graphite crucible in the absence of said sample by heating said graphite crucible up to a first temperature;
- degassing a flux metal in said graphite crucible in the absence of said sample by heating said flux metal at a second temperature that is lower than said first temperature;
- melting said sample in said graphite crucible in the presence of said flux metal by heating said sample at a third temperature that is lower than said second temperature; and
- extracting an element in a gaseous form from said sample by heating said graphite crucible to a fourth temperature that is higher than said third temperature.

7. The method of elemental analysis according to claim 6 wherein the step of heating said graphite crucible includes the step of directly heating an outside crucible which thereby indirectly heats an inside crucible.

8. The method of elemental analysis according to claim 6 wherein the step of degassing said double graphite crucible occurs in the absence of said flux metal.

9. The method of elemental analysis according to claim 6 further including the step of purging an environment of gasses generated during the steps of degassing said double graphite crucible and said flux metal.

10. The method of elemental analysis according to claim 6 wherein said sample is silicon containing oxygen, said flux metal is made of nickel and tin, said first temperature is about 2,900° C., said second temperature is about 2,600° C., said third temperature is about 1,500° C., and said fourth temperature is about 2,400° C.

11. A method of oxygen analysis utilizing a heat melting type gas extraction apparatus, comprising the steps of:
- indirectly heating an inside crucible of a double graphite crucible within said extraction apparatus;
- lowering a temperature of said double graphite crucible in a step-wise manner to degas a flux metal and melt a sample; and
- raising a temperature of said double graphite crucible to produce a sample gas from said sample.

12. The method of oxygen analysis according to claim 11 wherein the step of indirectly heating said inside crucible includes the step of producing carbon monoxide gas from said double graphite crucible in the absence of said sample and said flux metal.

13. The method of oxygen analysis according to claim 12 wherein the step of degassing said flux metal occurs before and separately from the step of melting said sample.

14. The method of oxygen analysis according to claim 13 further including the step of discharging gasses produced during the steps of heating said inside crucible and degassing said flux metal, said step of discharging occurring prior to the step of producing said sample gas.

15. The method of oxygen analysis according to claim 14 wherein the steps of heating said inside crucible and degassing said flux metal includes the step of extracting oxygen from said inside crucible and said flux metal.

16. The method of oxygen analysis according to claim 15 wherein said temperature is lowered from about 2,900° C. to about 1,500° C.

* * * * *